(12) United States Patent
Lee et al.

(10) Patent No.: US 12,327,275 B2
(45) Date of Patent: *Jun. 10, 2025

(54) METHOD, SYSTEM, AND NON-TRANSITORY COMPUTER-READABLE MEDIUM FOR ASSOCIATING TASTE WITH CONSUMABLE RECORDS

(71) Applicant: MYFITNESSPAL, INC., San Francisco, CA (US)

(72) Inventors: Chul Lee, San Francisco, CA (US); Kyler Eastman, Austin, TX (US); Patrick Howell, Austin, TX (US); Layla Martin, San Francisco, CA (US); Hesamoddin Salehian, San Francisco, CA (US); Joohyun Kim, San Francisco, CA (US)

(73) Assignee: MyFitnessPal, Inc., Austin, TX (US)

( * ) Notice: Subject to any disclaimer, the term of this patent is extended or adjusted under 35 U.S.C. 154(b) by 865 days.

This patent is subject to a terminal disclaimer.

(21) Appl. No.: 17/118,279

(22) Filed: Dec. 10, 2020

(65) Prior Publication Data

US 2021/0142367 A1 May 13, 2021

Related U.S. Application Data

(63) Continuation of application No. 15/215,861, filed on Jul. 21, 2016, now Pat. No. 10,878,458.

(51) Int. Cl.
*G06Q 30/0601* (2023.01)
*G16H 10/60* (2018.01)
*G16H 20/60* (2018.01)

(52) U.S. Cl.
CPC ......... *G06Q 30/0631* (2013.01); *G16H 10/60* (2018.01); *G16H 20/60* (2018.01)

(58) Field of Classification Search
CPC . G06Q 30/0631; G06Q 30/0601–0643; G06Q 30/0269
(Continued)

(56) References Cited

U.S. PATENT DOCUMENTS

2013/0339179 A1* 12/2013 Pickelsimer ....... G06Q 30/0631
705/26.7
2014/0255882 A1* 9/2014 Hadad ................ G09B 19/0092
434/127
(Continued)

FOREIGN PATENT DOCUMENTS

WO 2007023619 A1 3/2007

OTHER PUBLICATIONS

Pouladzadeh, P., et al., "Measuring Calorie and Nutrition From Food Image," in IEEE Transactions on Instrumentation and Measurement, vol. 63, No. 8, pp. 1947-1956, doi: 10.1109/TIM.2014.2303533 (Year: 2014).*
(Continued)

*Primary Examiner* — Kelly S. Campen
*Assistant Examiner* — Katherine A Barlow
(74) *Attorney, Agent, or Firm* — Maginot, Moore & Beck, LLP

(57) ABSTRACT

A method for operating a health tracking system, a health tracking system, and non-transitory computer-readable medium for operating a health tracking system are disclosed. The method comprises receiving a data record comprising at least a descriptive string and nutritional data regarding a consumable item to which the data record corresponds; determining a taste associated to the consumable item based on an evaluation of at least one of: (i) the descriptive string, and (ii) the nutritional data; and associating the determined taste with the data record in a database.

20 Claims, 11 Drawing Sheets

(58) Field of Classification Search
USPC .................................................... 705/26.7
See application file for complete search history.

(56) References Cited

U.S. PATENT DOCUMENTS

| | | | | |
|---|---|---|---|---|
| 2014/0280226 | A1* | 9/2014 | Wilson .................. | G06N 3/063 707/754 |
| 2014/0324607 | A1 | 10/2014 | Frehn et al. | |
| 2015/0235136 | A1 | 8/2015 | Dillon et al. | |
| 2015/0276700 | A1 | 10/2015 | Goel et al. | |
| 2015/0294225 | A1 | 10/2015 | Takei et al. | |
| 2016/0005097 | A1* | 1/2016 | Hsiao ................ | G06Q 30/0631 705/26.7 |
| 2016/0012513 | A1* | 1/2016 | Martinez ............... | G06Q 50/12 705/15 |
| 2016/0103910 | A1 | 4/2016 | Kim et al. | |
| 2016/0171514 | A1* | 6/2016 | Frank ..................... | G06Q 30/02 705/7.29 |
| 2017/0053362 | A1 | 2/2017 | Galarraga et al. | |
| 2017/0249445 | A1* | 8/2017 | Devries ................. | A61B 5/145 |

OTHER PUBLICATIONS

Temussi, P. A., "The good taste of peptides" J. Pept. Sci. 2012; vol. 18: p. 73â82. (Year: 2012).*
Berrueta, L., et al. "Supervised pattern recognition in food analysis," Journal of Chromatography A, vol. 1158, Iss. 1-2, pp. 196-214 , ISSN 0021-9673,https://doi.org/10.1016/j.chroma.2007.05.024. (Year: 2007).*
Ahn, Ahnert and Barabasi, Flavor Network and the Principles of Food Pairing, Scientific Reports, 2011, 1.
Breiman, Random Forests, Mach. Learn., Oct. 2001, 45(1):5-32.
Burger, Cornier, Ingebrigtsen and Johnson, Assessing Food Appeal and Desire to Eat; the Affects of Portion Size & Energy Density; International Journal of Behavioral Nutrition and Physical Activity, 2011, 8(1):101.
Cox, Moore, Vallis and Mela, Sensory and Hedonic Associations with Macronutrient and Energy Intakes of Lean and Obese Consumers, International Journal of Obesity and Related Metabolic Disorders; Journal of the International Association for the Study of Obesity, 1999, 23( 4): 403-410.
Dasarathy, Nearest Neighbor (NN) Norms: Nn Pattern Classification Techniques, IEEE Computer Society Press Tutorial, IEEE Computer Society Press, 1991.
Donaldson, Benneti, Baic, and Melichar, Taste and weight: is there a link? American Journal of Clinical Nutrition, Sep. 2009, 90(3):800S-803S.
Drewnoski and Monsivais, Present Knowledge in Nutrition, chapter 60. Taste and Food Choices, 2012, pp. 1027-1041. John Wiley & Sons, Inc, 10 edition.
Drewnowski, Brunzell, Sande, Iverius and Greenwood, Sweet tooth reconsidered: taste responsiveness In human obesity. Physiology & Behavior, 1985, 35(4):617-622.
Drewnoski, Kurth, Holden-Wiltse and Saari, Food preferences in human obesity: carbohydrates versus fats., Appetite, 1992, 18(3): 207-221.
Gearhardt, Rizk and Treat, The association of food characteristics and individual differences with ratings of craving and liking., Appetite, 2104, 79:166-173.

Glanz, Basil, Mai Bach, Goldberg and Snyder, Why americans eat what they do: Taste,nutrition, cost, convenience, and weight controlconcerns as influences on food consumption., Journal of the American Dietetic Association, Oct. 1998, 98(10):1118-1126.
Hastie, Tibshirani and Friedman, The Elements of Statistical Learning. Springer Series in Statistics., 2001, Springer New York Inc., New York, Ny, USA.
Keskitalo, Tuorila, Spector, Cherkas, Knmpilia, Kaprio, Silventoinen and Perola, The three-factor eating questionnaire, body mass index, and responses to sweet and salty fatty foods: a twin study of genetic and environmental associations., The American journal of clinical nutrition, 2008, 8(2):263-271.
Krebs, The gourmet ape: evolution and human food preferences., American Journal of Clinical Nutrition, Sep. 90(3).
Maffies, Grezzani, Perrone, Del Giudice, Saggese and Tato, Could the savory taste of snacks be a further risk factor for overweight in children? Journal of pediatric gastroenterology and nutrition, 2008, 46(4):429-437.
Matsunga, Doman, Hirayama, Ide, Deguchi, Murase, Tastes and textures estimation of foods based on the analysis of its ingredients list and image., In New Trends in Image Analysis and Processing-ICIAP 2015 Workshops, 2015, pp. 326-333, Springer.
Mikolov, Sutskever, Chen, Corrado and Dean, Efficient estimation of word representations in vector space., In Proceedings of Workshop at ICLR, 2013.
Mojet, Heidema and Christ-Hazelhof, Taste perception with age: Generic or specific losses in supra-threshold intensities of five taste qualities?, Chemical Senses, Jun. 28(5).
Nestle, Wing, Birch, Disogra, Drewnowski, Middleton Sigman-Grant, Sobal, Winston and Economos, Behavioral and social influences on food choice., Nutrition reviews, 1998, 56{5):50-64.
Ouwehand and Papies, Eat it or beat it. the differerential effects of food temptations on overweight and normal-weight restrained eaters., Appetite, 2010, 55(1):56-60.
Pepino, Finkbeiner, Beauchamp and Mennella, Obese women have lower monosodium glutamate taste sensitivity and prefer higher concentrations than do normal-weight women., Obesity, 2010, 18{5):959-965.
Sagioglou and Greitemeyer, Individual differences in bitter taste preferences are associated with antisocial personality traits. Appetite, 2016, 96:299-308.
Teng, Lin and Adamic, Recipe recommendation using ingredient networks. In Proceedings of the 4th Annual ACM Web Science Conference, 2012, pp. 298-307. ACM.
Togo, Osler, Sorenson and Heitmann, Food intake patterns and body mass index in observational studies International journal of obesity and related metabolic disorders: journal of the International Association for the Study of Obesity, 2001, 25(12):1741-1751.
Tucker, Edlinger, Craig and Maties, Associations between bmi and fat taste sensitivity in humans. Chemical senses, 2014, 39(4):349-357.
U.S. Department of Agriculture, Agricultural Research Service. USDA National Nutrient Database for Standard Reference, Release 27. 2014_ Nutrient Data Laboratory Home Page, http://www.ars.usda.gov/ba/bhnrc/ndl.
Wang, Kumar, Thome, Cord and Precioso, Recipe recognition with large multimodal food dataset In Multimedia & Expo Workshops (ICMEW), 2015 IEEE International Conference on, 2015, pp. 1-6. IEEE.

* cited by examiner

METHOD, SYSTEM, AND NON-TRANSITORY COMPUTER-READABLE MEDIUM FOR ASSOCIATING TASTE WITH CONSUMABLE RECORDS

CROSS-REFERENCE TO RELATED APPLICATIONS

This application is a continuation of and claims the benefit of U.S. patent application Ser. No. 15/215,861, filed Jul. 21, 2016, the entire contents of which are incorporated herein by reference.

COPYRIGHT

A portion of the disclosure of this patent document contains material that is subject to copyright protection. The copyright owner has no objection to the facsimile reproduction by anyone of the patent document or the patent disclosure, as it appears in the Patent and Trademark Office patent files or records, but otherwise reserves all copyright rights whatsoever.

FIELD

The method and apparatus disclosed in this document relates health and fitness tracking systems and, more particularly, to associating a taste with food and other consumable records in a database.

BACKGROUND

In recent years, health and fitness tracking applications that track food consumption have become very popular. Food consumption is important to a healthy lifestyle and is known to be related to various health conditions, such as diabetes and obesity to name a few. Health and fitness tracking applications allow users to set and achieve personalized health goals by tracking the foods and beverages that they consume. These applications enable users to gain insights that help them make smarter choices and create healthier habits.

Although many factors like colors, texture, temperature, and crushing sound play an important role in food sensation and consumption, it is strongly believed that food taste is one of the most important factors related to palatability, as well as to overall food consumption behavior. More specifically, taste is one of the primary drivers of food choice. Accordingly, any attempt to guide users towards healthier eating habits requires a clear picture of food tastes both on the individual and aggregate levels.

Hence, it would be advantageous to provide a method for predicting a taste of a food item and automatically labeling food items in a database with the predicted tastes. It would also be advantageous if the method is easily scalable for very large databases and robust enough to handle user-generated records having potentially inaccurate information.

SUMMARY

In accordance with one exemplary embodiment of the disclosures, a method of operating a health tracking system is disclosed. The method comprises receiving a data record comprising at least a descriptive string and nutritional data regarding a consumable item to which the data record corresponds; determining a taste associated to the consumable item based on an evaluation of at least one of: (i) the descriptive string, and (ii) the nutritional data; and associating the determined taste with the data record in a database.

Pursuant to another exemplary embodiment of the disclosures, a health tracking system is disclosed. The system comprises a database configured to store a plurality of data records, each of the plurality of data records comprising at least a descriptive string and nutritional data regarding the consumable item to which the data record corresponds; and a data processor in communication with the database, the data processor being configured to (i) receive one or more of the plurality of data records from the database, and (ii) determine a taste aspect for the consumable item to which each of the received ones of the one or more of the plurality of data records corresponds, the determination being based on an evaluation of at least one of the descriptive string and the nutritional data.

In accordance with yet another exemplary embodiment, a non-transitory computer-readable medium for a health tracking system is disclosed. The computer-readable medium has a plurality of instructions stored thereon that, when executed by a processor, cause the processor to: receive a plurality of data records from a database, the plurality data records each comprising a descriptive string and nutritional data regarding the respective corresponding consumable; determine a taste for each of the respective corresponding consumables of the plurality of data records based on at least one of (i) the descriptive string and (ii) the nutritional data thereof; and store the determined tastes in the database associated to the respective ones of the plurality of data records.

BRIEF DESCRIPTION OF THE DRAWINGS

The foregoing aspects and other features of a health and fitness tracking system are explained in the following description, taken in connection with the accompanying drawings.

Figure 1:
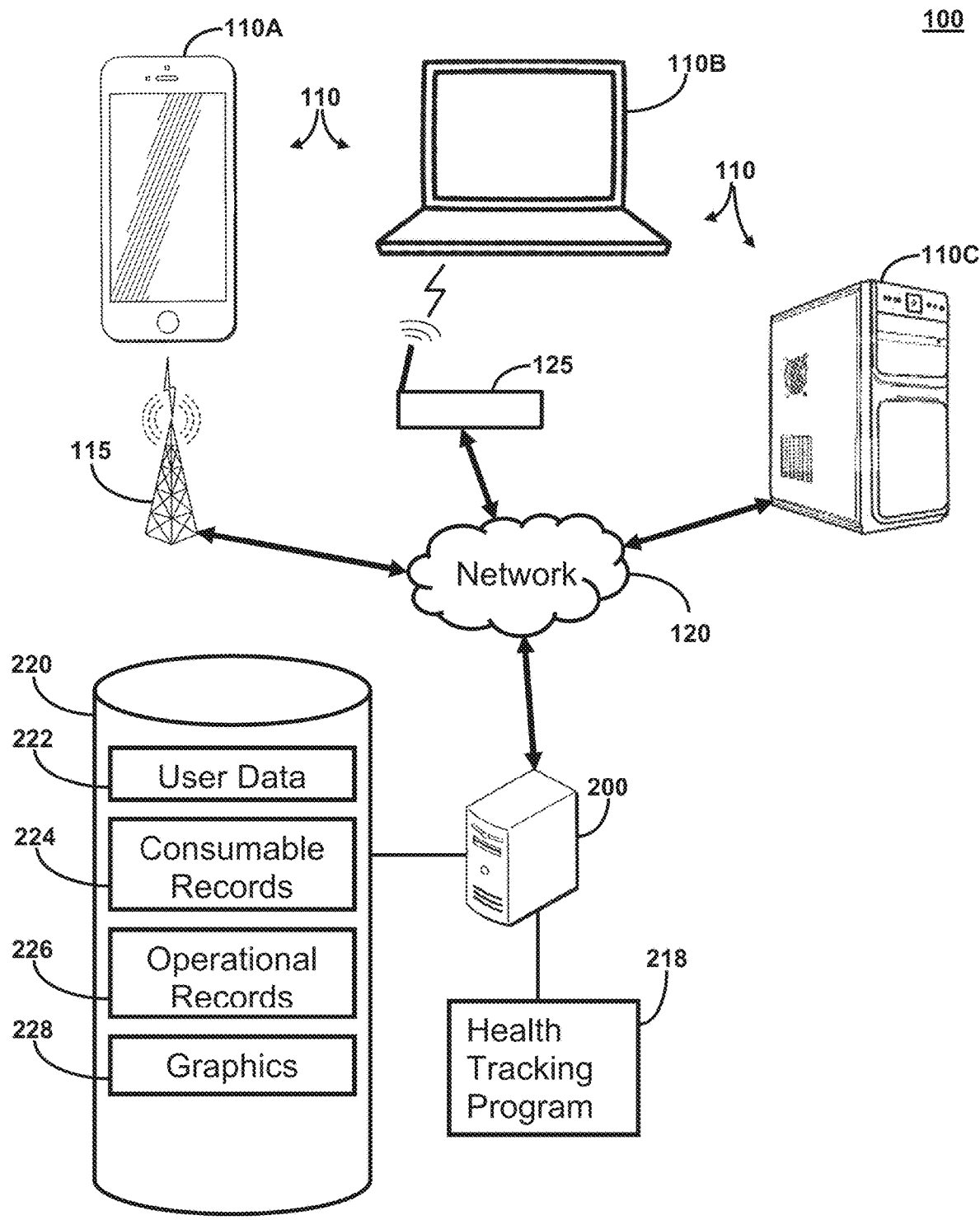
FIG. 1 shows a health tracking system.

All Figures © Under Armour, Inc. 2016. All rights reserved.

DETAILED DESCRIPTION

For the purposes of promoting an understanding of the principles of the disclosure, reference will now be made to the embodiments illustrated in the drawings and described in the following written specification. It is understood that no limitation to the scope of the disclosure is thereby intended. It is further understood that the present disclosure includes any alterations and modifications to the illustrated embodiments and includes further applications of the principles of the disclosure as may normally occur to one skilled in the art which this disclosure pertains.

Disclosed embodiments include systems, apparatus, and methods associated with health and fitness tracking in general, and in particular a system for associating a taste with food records in a database.

In the following detailed description, reference is made to the accompanying drawings which form a part hereof wherein like numerals designate like parts throughout, and in which is shown, by way of illustration, embodiments that may be practiced. It is to be understood that other embodiments may be utilized, and structural or logical changes may be made without departing from the scope of the present disclosure. Therefore, the following detailed description is not to be taken in a limiting sense, and the scope of embodiments is defined by the appended claims and their equivalents.

Aspects of the disclosure are disclosed in the accompanying description. Alternate embodiments of the present disclosure and their equivalents may be devised without parting from the spirit or scope of the present disclosure. It is noted that any discussion herein regarding "one embodiment", "an embodiment", "an exemplary embodiment", and the like indicate that the embodiment described may include a particular feature, structure, or characteristic, and that such particular feature, structure, or characteristic may not necessarily be included in every embodiment. In addition, references to the foregoing do not necessarily comprise a reference to the same embodiment. Finally, irrespective of whether it is explicitly described, one of ordinary skill in the art will readily appreciate that each of the particular features, structures, or characteristics of the given embodiments may be utilized in connection or combination with those of any other embodiment discussed herein.

Various operations may be described as multiple discrete actions or operations in turn, in a manner that is most helpful in understanding the claimed subject matter. However, the order of description is not to be construed as to imply that these operations are necessarily order dependent. In particular, these operations may not be performed in the order of presentation. Operations described may be performed in a different order than the described embodiment. Various additional operations may be performed and/or described operations may be omitted in additional embodiments.

For the purposes of the present disclosure, the phrase "A and/or B" means (A), (B), or (A and B). For the purposes of the present disclosure, the phrase "A, B, and/or C" means (A), (B), (C), (A and B), (A and C), (B and C), or (A, B and C).

The terms "comprising," "including," "having," and the like, as used with respect to embodiments of the present disclosure, are synonymous.

As used herein, the term "consumable" as refers to foods, beverages, dietary supplements, vitamin supplements, medication, and other items for consumption. As used herein, the term "consumable record" refers to a database record that relates to a particular consumable. Each consumable record comprises a plurality of data fields that relate to a particular consumable. In some embodiments, the consumable record includes a description field that includes data, such as a text string, that identifies or describes the particular consumable. In some embodiments, each consumable record includes fields for caloric content, macronutrients, micronutrients, serving size, and other nutrition and health information.

Health Tracking System

With reference to FIG. 1, an exemplary embodiment of a health tracking system 100 including automatic taste prediction and labeling is shown. In the illustrated embodiment, the health tracking system 100 includes a plurality of health tracking devices 110 in communication with a system server 200 or other data processing system over a network 120 such as, e.g. the Internet.

The server 200 comprises a computerized device or data processing system configured to run one or more software applications on a processor thereof (e.g. the network-side health tracking program 218). The server 200 of the present embodiment is further configured to receive a plurality of consumable records which include caloric and nutritional contents of a respective plurality of consumable items which are entered at the health tracking devices 110, other consumer devices, and/or provided from one or more manufacturing or distributing entities. The consumable records are stored at a storage apparatus or memory of the server 200 (e.g., consumable records 224).

The storage apparatus or memory is configured to store instructions including a network-side health tracking program 218 (which may also be referred to herein as the "health tracking application"), as well as a database 220 accessible by at least the health tracking program 218. The database 220 includes user data 222, consumable records 224, operational records 226, and graphics 228. Alternatively, the server 200 may be in communication with a separate storage entity (not shown) for storage thereof. The server 200 is configured to automatically determine a taste for a consumable corresponding to each of the consumable records 224, as discussed in further detail elsewhere herein. The determined tastes are stored in the database 220 in association with corresponding consumable records 224. In one variant, each of the consumable records 224 advantageously includes a label which identifies a "taste" for the corresponding consumable. The health tracking system 100 is configured to utilize these so-called "taste labels" to enable functionalities and features discussed in further detail herein.

The health tracking devices 110 (which may also be referred to herein as "health and fitness tracking devices") comprise any number of computerized apparatus which include a user interface such as e.g., a smartphone 110A, laptop computer 110B, a tablet computer, a desktop computer 110C, or other such device. In at least one embodiment, the user interface may comprise an LCD touch screen or the like, a mouse or other pointing device, a keyboard or other keypad, speakers, and a microphone, as will be recognized by those of ordinary skill in the art. The user interface provides the user with any of various health, fitness and activity related data such as food and nutritional consumption, calorie expenditure, sleep metrics, weight, body fat, heart rate, distance travelled, steps taken, etc. In order to connect to the network 120, the health tracking devices 110 are generally configured to utilize any of various wired or wireless communications components, infrastructures and systems, such as cell towers 115 of a mobile telephony network, wireless routers 125, Bluetooth®, near field communication (NFC), or physical cables. Health tracking devices 110 may use data collected from sensors associated to or in communication with the health tracking device 110, such as heart rate monitors, step counters, stair counters, global positioning system ("GPS") tracking devices, as well as various other motion tracking and biometric monitoring devices; alternatively, or in addition, a user may manually enter health related data. Such sensors allow the user to easily track and automatically log activity and/or consumption information with the health tracking device.

The health tracking devices 110 are configured to communicate with the system server 200 in order to enable: accessing and searching of the consumable records 224 stored thereat, display of the consumable records, provide additional records, and/or enable the user to select individual ones of the displayed consumable records for the purposes of caloric and nutritional logging. In one embodiment, foregoing functions are performed via execution of one or more software applications at the server 200 (i.e., server or network-side applications) in communication with one or more complementary software applications at the health tracking devices 110 (i.e., client-side applications). For example, the health tracking program 218, running on the processor (of the server 200) may be utilized to accomplish the foregoing, as explained in further detail below. A client-side software application for performing various functions necessary for the herein disclosed concepts may also be utilized (see health tracking application 316 of FIG. 3, discussed below).

System Server

Figure 2:
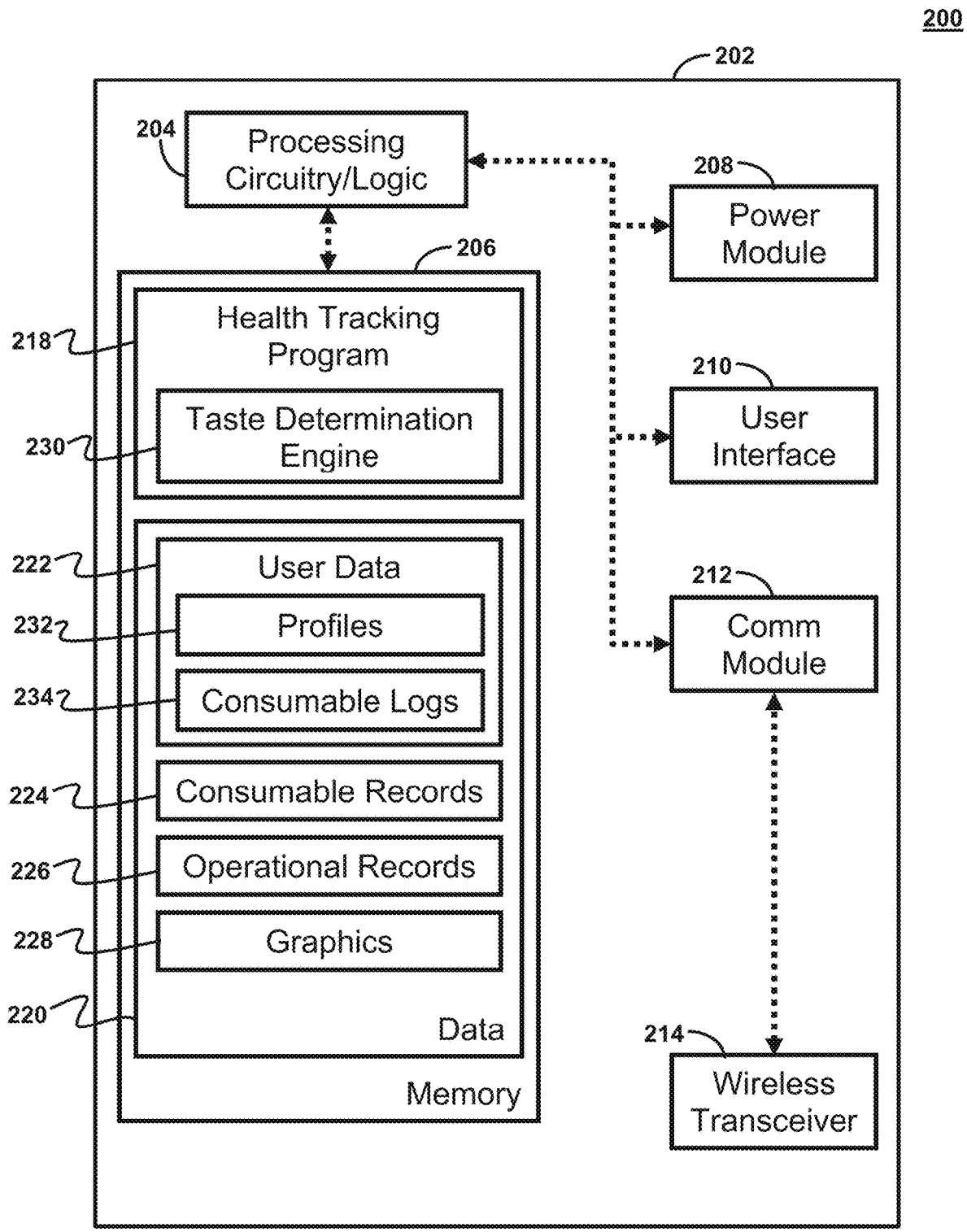
FIG. 2 shows a system server or data processing system of the health tracking system of FIG. 1.

With reference now to FIG. 2, a block diagram of an exemplary embodiment of the system server 200 of FIG. 1 is shown. It is appreciated that the embodiment of the system server 200 shown in FIG. 2 is only one exemplary embodiment of a system server 200. As such, the exemplary embodiment of the system server 200 of FIG. 2 is merely representative of any of various manners or configurations of system servers or other data processing systems that are operative in the manner set forth herein.

The system server 200 of FIG. 2 is typically provided in a housing, cabinet or the like 202 that is configured in a typical manner for a server or related computing device. In one embodiment, the system server 200 includes processing circuitry/logic 204, memory 206, a power module 208, a user interface 210, a network communications module 212, and a wireless transceiver 214.

The processing circuitry/logic 204 is operative, configured and/or adapted to operate the system server 200 including the features, functionality, characteristics and/or the like as described herein. To this end, the processing circuitry/logic 204 is operably connected to the memory 206, the power module 208, the user interface 210, the network communications module 212, and the wireless transceiver 214. The memory 206 may be of any type of device capable of storing information accessible by the processor, such as a memory card, ROM, RAM, write-capable memories, read-only memories, hard drives, discs, flash memory, or any of various other computer-readable medium serving as data storage devices as will be recognized by those of ordinary skill in the art. The memory 206 is configured to store instructions including a network-side health tracking application 218 for execution by the processing circuitry/logic 204, as well as a database 220 for use by at least the health tracking program 218. The database 220 includes user data 222, consumable records 224, operational records 226, and graphics 228. As discussed in greater detail below, the health tracking application 218 includes a taste determination engine 230 configured to determine tastes for consumables and provide taste labels that are stored in association with each consumable record 224.

With continued reference to FIG. 2, the power module 208 of the system server 200 is operative, adapted and/or configured to supply appropriate electricity to the system server 200 (i.e., including the various components of the system server 200). The power module 208 may operate on standard 120 volt AC electricity, but may alternatively operate on other AC voltages or include DC power supplied by a battery or batteries.

The network communication module 212 of the system server 200 provides an interface that allows for communication with any of various devices using various means. In particular, the network communications module 212 includes a local area network port that allows for communication with any of various local computers housed in the same or nearby facility. In some embodiments, the network communications module 212 further includes a wide area network port that allows for communications with remote computers over the Internet (e.g., network 120 of FIG. 1). Alternatively, the system server 200 communicates with the network 120 via a modem and/or router of the local area network. In one embodiment, the network communications module is equipped with a Wi-Fi transceiver 214 or other wireless communications device. Accordingly, it will be appreciated that communications with the system server 200 may occur via wired communications or via the wireless communications. Communications may be accomplished using any of various known communications protocols. In the embodiment of FIG. 2, the wireless transceiver 214 may be a Wi-Fi transceiver, but it will be recognized that the wireless transceiver may alternatively use a different communications protocol.

The system server 200 may be accessed locally by an authorized user (i.e., an administrator or operator). To facilitate local access, the system server 200 includes an interactive user interface 210. Via the user interface 210, the health tracking application 218, and may collect data from and store data to the memory 206. In at least one embodiment, the user interface 210 may suitably include an LCD touch screen or the like, a mouse or other pointing device, a keyboard or other keypad, speakers, and a microphone, as will be recognized by those of ordinary skill in the art. Accordingly, the user interface 210 is configured to provide an administrator or other authorized user with access to the memory 206 and allow the authorized user to amend, manipulate and display information contained within the memory.

As mentioned above, the memory 206 includes various programs and other instructions that may be executed by the processor circuitry/logic 204. In particular, the memory 206 of the system server 200 of FIG. 2 includes the health tracking program 218 (which may also be referred to herein as a "health tracking application"). The health tracking program 218 is configured to cause the system server 200 to enable a user to obtain nutritional data related to any of various consumables. Execution of the health tracking application 218 by the processor circuitry/logic 204 results in signals being sent to and received from the user interface 210 and the communications module 212 (for further delivery to a user device such as a health tracking device 110), in order to allow the user receive and update various aspects of the consumable records 224. The network-side health tracking application 218 is configured to provide various graphical views and screen arrangements to be displayed to a user on a health tracking device 110.

The user data 222 includes at least user profiles 232 and corresponding consumable logs 234. The user profiles 232 include a profile data for each user of the health tracking system 100. Each user profile includes demographic information for the users such as name, age, gender, height, weight, performance level (e.g., beginner, intermediate, professional, etc.) and/or other information for the user. In at least one embodiment, the consumable logs 234 include a consumable diary/log for each user. The consumable diary/log allows the user to track consumables that are consumed by the user over a period of days and any nutritional data associated with the food consumed. For example, the consumable diary/log may allow the user to enter particular consumable that is consumed by the user and keep track of the associated calories, macronutrients, micronutrients, sugar, fiber, and/or any of various other nutritional data associated with the consumables entered by the user in the consumable diary/log. In some embodiments, the user data 222 further includes various activity and fitness data collected by sensors (not shown) associated with the health tracking devices 110.

In an alternative embodiment, the foregoing profile data may be stored at a storage entity separate from yet in communication with the server 200. For example, a centralized server may be provided which is configured to store all data relating to an individual user in one storage area (including workout data, nutrition/consumption data, profile data, etc.).

A plurality of consumable records 224 are stored in the database 220. As discussed above, the term "consumable record" refers to a database record that relates to a particular consumable. In at least one embodiment, each consumable record comprises a plurality of data fields that related to a particular consumable. At least some consumable records 224 and/or fields are editable by users or may be created by users within the database 220 without the need for special authorization or privileges. In the disclosed embodiment, each of the consumable records includes a number of fields including, for example, a name for the consumable, summary information about the consumable, and detailed nutritional information about the consumable. Detailed information about a consumable may include one or more of: serving size, calories, ingredients, or any other nutritional information about the consumable. For example, the nutritional information may include information that may be provided on USDA food labels or state-regulated food labels (e.g., vitamin and mineral content, fat content, cholesterol content, protein content, sugar content, carbohydrate content, fiber content, organic contents, etc.). The summary information about the consumable may include some subset of the more detailed information about the consumable. For example, the summary information about the consumable may only include serving size and calorie information. The various fields of each consumable record may be populated by data from any user or third party data providers. Therefore, it will be recognized that in at least some embodiments, consumable records 224 may have been entered by any of various sources including an administrator or operator of the health tracking system 100, commercial food providers (e.g., food distributors, restaurant owners, etc.), and/or users of the health tracking system 100.

The operational records 226 include current and historical data stored by the system server 200 in association with operation of the system server 200, execution of the health tracking application 218, and/or manipulation of data 220 within the memory 206. For example, the operational records 226 may include information concerning amendments made to any of various consumable records 224. The operational records 226 may also include other information related to the control and operation of the system server 200, including statistical, logging, licensing, and historical information.

In one embodiment, graphical views 228 are provided at the server 200 which are pushed to the health tracking device 110 for display thereat of various screen arrangements, as shown in FIG. 1.

While the system server 200 has been explained in the foregoing embodiment as housing the health tracking program 218 and the various records and databases in the memory 206, it will be recognized that in other embodiments these components may be retained in other one or more remote locations in communication with the health tracking system 100. For example, in at least one embodiment, the consumable records 224 may be data retained by a database separate from the system server 200. Alternatively, the consumable records 224 or certain fields of the consumable records 224 are received from a third party database. In such embodiments, the health tracking application may utilize any number of application programming interfaces (APIs) to access the data in the third party databases and incorporate such information for use in the health tracking application 218, without local storage thereof. Accordingly, it will be recognized that the description of the system server 200 of FIG. 2 is but one exemplary embodiment of a data processing system that may be utilized by the health tracking system 100.

A computer program product implementing an embodiment disclosed herein may therefore comprise one or more computer-readable storage media storing computer instructions executable by a processor to provide an embodiment of a system or perform an embodiment of a method disclosed herein. Computer instructions (e.g., the health tracking application 218 including the taste determination engine 230) may be provided by lines of code in any of various languages as will be recognized by those of ordinary skill in the art. A "non-transitory computer-readable medium" may be any type of data storage medium that may store computer instructions, including, but not limited to a memory card, ROM, RAM, write-capable memories, read-only memories, hard drives, discs, flash memory, or any of various other computer-readable medium.

Health Tracking Devices

With reference again to FIG. 1, the health tracking devices 110 may be provided in any of various forms. Examples of a health tracking devices 110 configured for use with the health tracking system 100 include a smartphone 110A, a laptop computer 110B, and a desktop computer 110C, as shown in FIG. 1, as well as various other electronic devices. Accordingly, it will be recognized that the health tracking devices 110 may comprise portable electronic devices such as the smartphone 110A or the laptop computer 110B, or stationary electronic devices such as the desktop computer 110C. Other examples of health tracking devices include, handheld or tablet computers, smart watches, portable media players, other wearable devices, or any of various other health tracking devices configured to receive entry of consumables (not shown).

In one embodiment, data entered at one device 110 may be provided to other ones of the user's devices 110. For example, data entered at the smart phone 110A may be provided to the desktop computer 110C and/or the laptop computer 110B for storage thereat. Alternatively, the data may be stored at a single network storage apparatus (not shown) having a dedicated portion of storage for records relating to the user and accessible by all of the user's devices 110.

Figure 3:
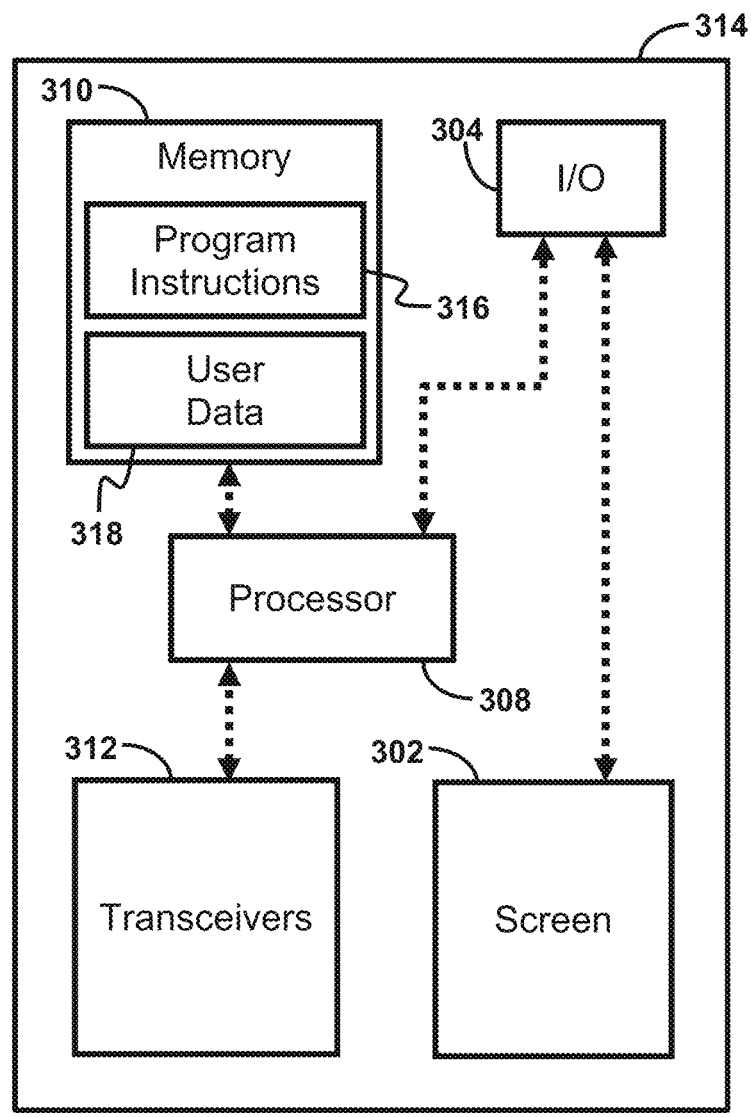
FIG. 3 shows a smartphone of the health tracking system of FIG. 1.

With reference now to FIG. 3, in at least one embodiment the health tracking device 110 is provided in the form of a smartphone 110A. The smartphone 110A includes a display screen 302, an input/output (I/O) interface 304, a processor 308, a memory 310, and one or more transceivers 312. The smartphone 110A also includes a protective outer shell or housing 414 designed to retain and protect the electronic components positioned within the housing 414. The smartphone 110A also includes a battery (not shown) configured to power the display screen 302, processor 308, transceivers 312 and various other the electronic components within the smartphone 110A.

The display screen 302 of the smartphone 110A may be an LED screen or any of various other screens appropriate for the personal electronic device. The I/O interface 304 of the smartphone 110A includes software and hardware configured to facilitate communications with the user. The I/O interface 304 is in communication with the display screen 302 and is configured to visually display graphics, text, and other data to the user via the display screen 302. As will be recognized by those of ordinary skill in the art, the components of the health tracking device 110 may vary depending on the type of display device used. Alternative health tracking devices, such as the laptop 110B and the desktop 110C, may include much of the same functionality and components as the smartphone 110A shown in FIG. 3, but may not include all the same functionality or components and/or may include others not listed.

The processor 308 of the smartphone 110A may be any of various processors as will be recognized by those of ordinary skill in the art. The processor 308 is in communication with the I/O interface 304, the memory 310, and the transceivers 312, and is configured to deliver data to and receive data from each of these components. The memory 310 is configured to store information, including data and instructions for execution by the processor 308. It will be recognized by those of ordinary skill in the art that a "processor" includes any hardware system, hardware mechanism or hardware component that processes data, signals or other information. A processor may include a system with a central processing unit, multiple processing units, dedicated circuitry for achieving functionality, or other systems.

The transceivers 312 may be any of various devices configured for communication with other electronic devices, including the ability to send communication signals and receive communication signals. The transceivers 312 may include different types of transceivers configured to communicate with different networks and systems. Such transceivers are well known and will be recognized by those of ordinary skill in the art.

In some embodiments, the transceivers 312 include at least one transceiver configured to allow the smartphone 110A to perform wireless communications with the cell towers 115 of the wireless telephony network, as will be recognized by those of ordinary skill in the art. The wireless telephony network may comprise any of several known or future network types. For example, the wireless telephony network may comprise commonly used cellular phone networks using CDMA, GSM or FDMA communication schemes, as well as various other current or future wireless telecommunications arrangements.

In some embodiments, the transceivers 312 include at least one transceiver configured to allow the smartphone 110A to communicate with any of various local area networks using Wi-Fi, Bluetooth® or any of various other communications schemes.

In some embodiments, the memory 310 includes program instructions for a graphical user interface configured to provide a client-side health tracking application 316. The memory 310 may further be configured to store certain user data 318, such as e.g., user gender, height, weight, user identifier, password, etc. Additionally, health related data (e.g., data collected from one or more sensors and/or manually entered) may be stored. The processor 308 is configured to read the program instructions from the memory 310 and execute the program instructions to provide the health tracking application 316 to the user so for the purpose of performing health and fitness related tasks for the user, including displaying, modifying, and analyzing the user data 318.

In at least one embodiment, the user data 318 includes a plurality of consumable records which serves as a log of consumables that have been consumed by the user for the purpose of caloric and nutritional tracking. That is to say, the client-side health tracking application 316 is configured to display consumable records and enable the user to select consumable records (from a plurality of records accessed via the network 120), those items that correspond to consumables that he or she has consumed are stored at the client-side for the purpose of logging the consumables in this embodiment. In another alternative, such log may be stored remote from the device and/or only kept at the device for a transitory period.

The memory 310 that retains the data and instructions may be of any type of device capable of storing information accessible by the processor, such as a memory card, ROM, RAM, write-capable memories, read-only memories, hard drives, discs, flash memory, or any of various other computer-readable medium serving as data storage devices as will be recognized by those of ordinary skill in the art. Portions of the system and methods described herein may be implemented in suitable software code that may reside within the memory as software or firmware. Alternatively, or in addition, the software (such as e.g., the client side health tracking program 316) may be downloaded from a network location, such as via the Internet.

Method of Predicting Taste for Consumable Records

Methods for operating the health tracking system 100 are described below. In particular, a method of associating taste information with food records is provided. In the description of the methods, statements that a method is performing some task or function refers to a controller or general purpose processor executing programmed instructions stored in non-transitory computer readable storage media operatively connected to the controller or processor to manipulate data or to operate one or more components in the health tracking system 100 to perform the task or function. Particularly, the processor circuitry/logic 204 of the system server 200 and/or the processor 308 of the smartphone 110A above may be such a controller or processor. Alternatively, the controller may be implemented with more than one processor and associated circuitry and components, each of which is configured to form one or more tasks or functions described herein. Additionally, the steps of the methods may be performed in any feasible chronological order, regardless of the order shown in the figures or the order in which the steps are described.

Figure 4:
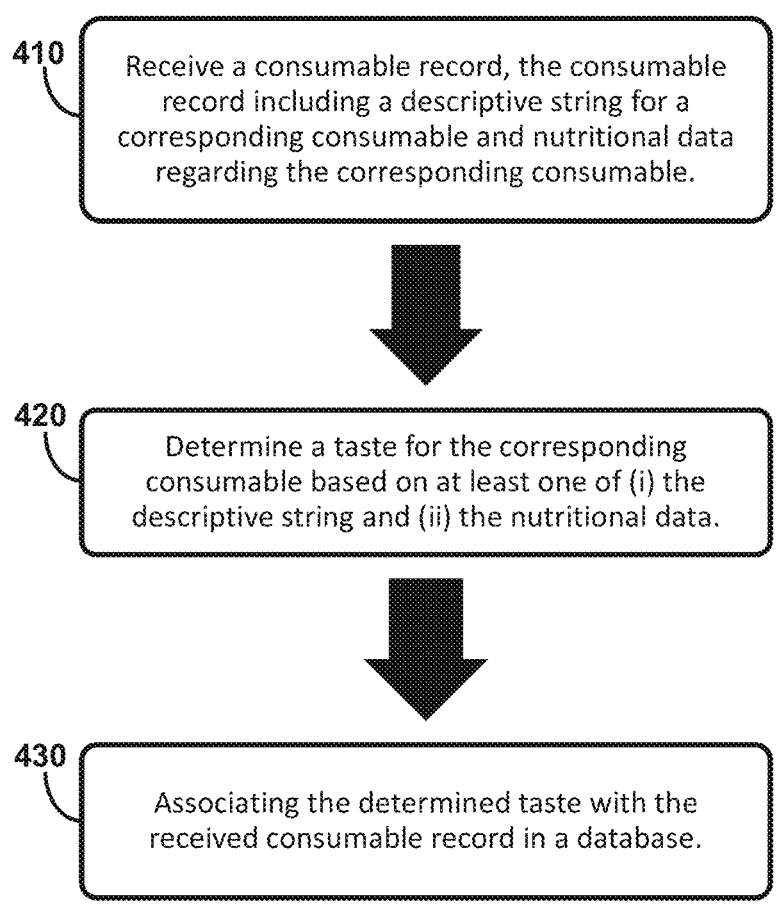
FIG. 4 shows a method of providing taste information for consumable records in a database.

FIG. 4 shows a method 400 of providing taste information for consumable records 224. The method 400 begins with a step of receiving a consumable record, the consumable record including a descriptive string for a corresponding consumable and nutritional data regarding the corresponding consumable (block 410). Particularly, with respect to the embodiments described in detail herein, the processing circuitry/logic 204 of the system server 200 is configured to receive or read a consumable record from the database 220. The received consumable record at least includes a descriptive string that provides a name for the consumable (e.g., "apple") and one or more nutritional data regarding a corresponding consumable. In a preferred embodiment, the nutritional data at least includes total caloric contents and macronutrient contents (i.e. fat content, carbohydrate content, protein content, etc.).

Next, the method 400 includes a step of determining a taste for the corresponding consumable based on at least one of (i) the descriptive string and (ii) the nutritional data (block 420). In one embodiment, the processing circuitry/logic 204 is configured to execute program instructions of the taste determination engine 230 to determine a taste for the consumable that corresponds to the received consumable record. The processing circuitry/logic 204 is configured to determine the taste for the consumable based on the descriptive string of the received consumable record and/or the one or more nutritional data of the received consumable record. In one embodiment, the taste is one or more of the following fundamental flavors: bitter, salty, umami (savory), sour, spicy, and sweet; however other aspects of taste and/or of consumable items may be determined using the herein disclosed methods and systems. Methods for determining a taste for a consumable are discussed in greater detail below.

Finally, the method 400 includes a step of associating the determined taste with the received consumable record in a database (block 430). Particularly, the processing circuitry/logic 204 is configured to store the determined taste for the consumable record in a data field of the database 220 or otherwise in association with the received consumable record (e.g., in a taste data field of the consumable record).

In many embodiments, the method 400 is repeated with respect to each consumable record 224 in the database 220 having the data in the fields required by the taste determination engine 230 for determining a taste of the corresponding consumable. In another embodiment, the method 400 is performed automatically after a new consumable record is generated by the health tracking system 100 or is otherwise received by the health tracking system 100. Alternatively, the method 400 may be performed on a periodic and/or scheduled basis to determine tastes for any newly added or modified consumable records in the database 220.

Taste Determination Engine

Figure 5:
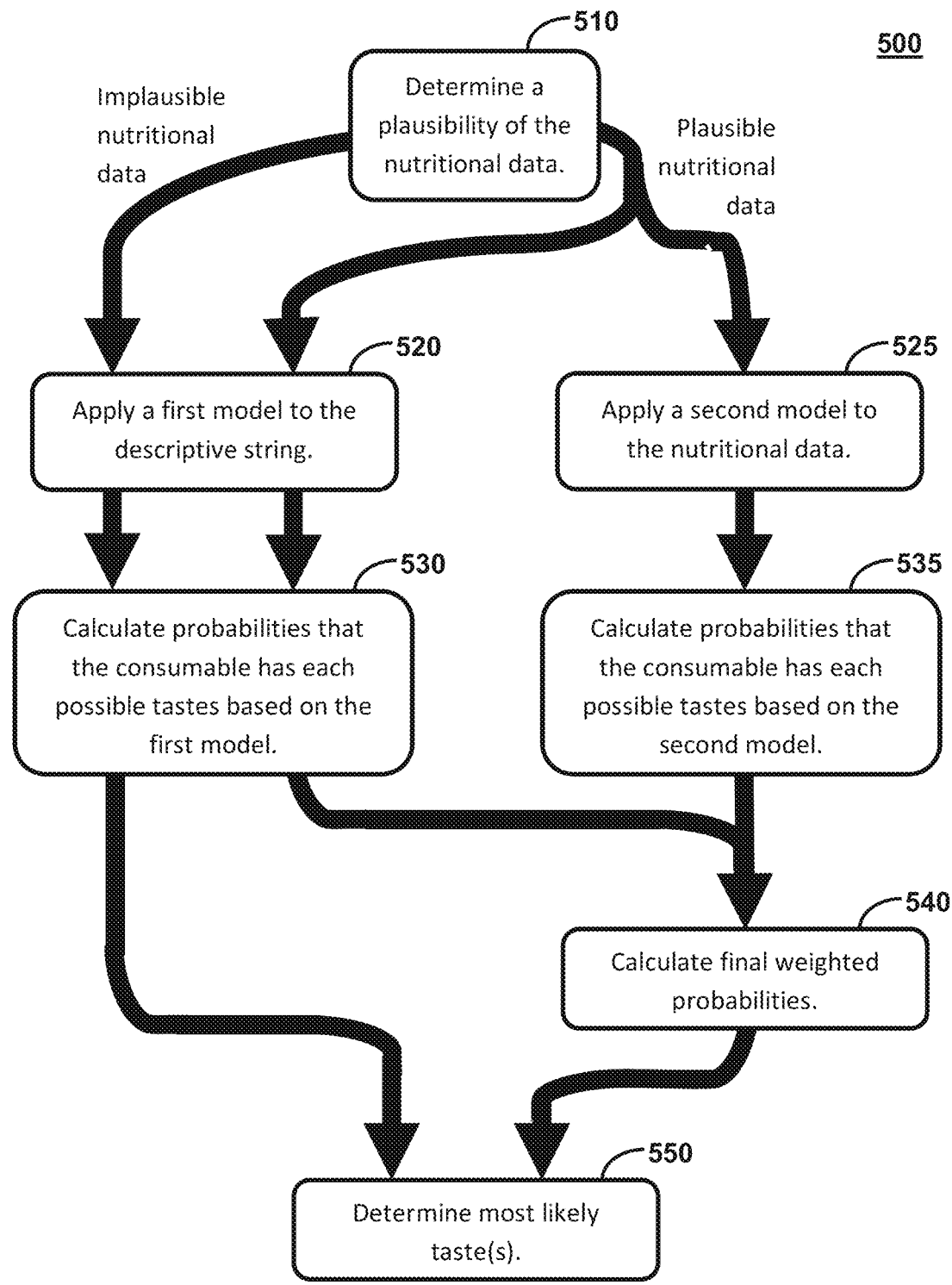
FIG. 5 shows a method for determining a taste of a consumable.

FIG. 5 shows a method 500 of determining a taste for a consumable based on data stored in the corresponding consumable record. The method 500 is one exemplary implementation of step 420 of the method 400 and an exemplary embodiment of the taste determination engine 230. However, it will be understood by a person having ordinary skill in the art that other methods and/or variations of this method are possible.

The method 500 begins by determining a plausibility or accuracy of the nutritional data of the consumable record (block 510). Particularly, with respect to the embodiments described in detail herein, the processing circuitry/logic 204 of the system server 200 is configured to determine if the nutritional data is plausible or accurate by performing one or more checks on the nutritional data. In one embodiment, the processing circuitry/logic 204 is configured to compare the total caloric content of the consumable to the macronutrient contents of the consumable to determine in the nutritional data is plausible or accurate. More particularly, it is known that fat has approximately 9 calories per gram, that protein has approximately 4 calories per gram, and that carbohydrates have 4 calories per gram. Accordingly, the nutritional data may be verified according to the equation: Total Calories 4*Protein+4*Carbohydrates+9*Fats. If the estimated macronutrient calories are roughly equal to the listed total caloric content within a predetermined threshold, then the processing circuitry/logic 204 is configured to determine that the nutritional data is plausible or accurate. However, if the estimated macronutrient calories differ from the listed total caloric content by more than a predetermined amount or percentage, then the processing circuitry/logic 204 is configured to determine that the nutritional data is implausible or inaccurate.

In some embodiments, additional checks are performed to determine the plausibility or accuracy of the nutritional data. Particularly, in one embodiment, the processing circuitry/logic 204 is configured to compare the descriptive string of consumable to the macronutrient contents. In certain limited circumstances, the descriptive string of the consumable may give important clues about whether the nutritional data are accurate. For example, if the descriptive string includes the phrase "protein shake" but the nutritional data indicates that the consumable has zero grams of protein, then it may be assumed that the nutritional data is incorrect or incomplete Similarly, if the descriptive string includes the phrase "fried" but the nutritional data indicates that the consumable has zero grams of fat, then it may be assumed that the nutritional data is incorrect or incomplete.

In further embodiments, the processing circuitry/logic 204 is configured to compare a serving size for the consumable with the nutritional contents of the consumable. Particularly, if the serving size is listed in terms of mass, then the serving size is greater than (or, at the very least, equal to) a sum of the masses of fat, protein, carbohydrates, and fiber. For example, if the serving size is "32 grams", but the nutritional data indicates that there are 22 grams of fat, 18 grams of protein, 29 grams of carbohydrates, and 4 grams of fiber per serving, then it may be assumed that the nutritional data is incorrect or incomplete. However, if the serving size is greater than the sum of the masses of fat, protein, carbohydrates, and fiber, then no inferences may be drawn regarding the accuracy of nutritional content. It is noted that this comparison may not be made if the serving size is listed in terms of volume (e.g., fluid ounces).

If it is determined that the nutritional data is implausible or inaccurate, then the method 500 continues with a step of applying a first model to the descriptive string (block 520). Particularly, the processing circuitry/logic 204 is configured to ignore the nutritional data and apply a text-based model (described in further detail below with respect to FIG. 6) for predicting a taste of the consumable using the descriptive string. The processing circuitry/logic 204 is configured to use the text-based model to calculate a set of probabilities that the consumable has each of the possible tastes (block 530). In one embodiment, the possible tastes include bitter, salty, umami (savory), sour, spicy, and sweet. However, other tastes or consumable item related aspects may be utilized with equal success. Table 1, below, shows an exemplary sets of probabilities for several consumables:

TABLE 1

| Descriptive String (i.e. Food Name) | Probabilities | | | | | |
|---|---|---|---|---|---|---|
| | Bitter | Salty | Umami | Sour | Spicy | Sweet |
| Instant Coffee + 1 Sugar + 25 ml Skim Milk | 0.8079 | 0.0000 | 0.0000 | 0.0000 | 0.0000 | 0.1921 |
| Caramel Popcorn | 0.0000 | 0.4298 | 0.0000 | 0.0319 | 0.0000 | 0.5383 |
| Fruit Smoothie | 0.0000 | 0.0000 | 0.0000 | 0.1379 | 0.0000 | 0.8621 |
| Spices - Pepper, red or cayenne | 0.0274 | 0.0000 | 0.2119 | 0.0290 | 0.5532 | 0.1786 |
| Pepperoni Pizza | 0.0000 | 0.1834 | 0.6806 | 0.0000 | 0.0579 | 0.0786 |
| Gummi Worms | 0.0000 | 0.0000 | 0.0000 | 0.1456 | 0.0000 | 0.8544 |
| Coke Zero 12 oz | 0.0000 | 0.0000 | 0.0000 | 0.0000 | 0.0000 | 1.0000 |

If it is determined that the nutritional data is plausible or accurate, then the method 500 continues with steps of applying a first model to the descriptive string (block 520) and applying a second model to the nutritional data (block 525). Particularly, the processing circuitry/logic 204 is configured to apply the text-based model for predicting a taste of the consumable using the descriptive string and apply a nutrient-based model (described in further detail below with respect to FIG. 7) for predicting a taste of the consumable using the nutritional data. The processing circuitry/logic 204 is configured to use the text-based model to calculate a first set of probabilities that the consumable has each of the possible tastes (block 530). Additionally, the processing circuitry/logic 204 is configured to use the nutrient-based model to calculate a second set of probabilities that the consumable has each of the possible tastes (block 535).

In the case in which the nutritional data is plausible or accurate and in which both models are used to calculate separate sets of probabilities, the method 500 continues with a step of calculating final weighted probabilities (block 540). Particularly, the processing circuitry/logic 204 is configured to calculate a set of final probabilities based on a weighted average of the first set of probabilities provided by the text-based model and the second set of probabilities provided by the nutrient-based model. In one embodiment, the weighting comprises a predetermined or fixed weighting. However, in other embodiments, the weighting is dependent on the first set of probabilities calculated with respect to the text-based model.

For example, in one embodiment wherein the weighting is dependent on the first set of probabilities calculated with respect to the text-based model, if the text-based model yields over a 50% probability that the consumable is either "sour" or "spicy", then the second set of probabilities calculated with respect to the nutrient-based model are ignored or minimally weighted because nutrient content is minimally predictive of sour and/or spicy tasting consumables. If the text-based model yields over 50% probability that the consumable is any of "bitter", "salty", "umami", or "sweet", then the second set of probabilities calculated with respect to the nutrient-based model are moderately weighted (e.g., with 30% weighting). Additionally, if the text-based model is relatively non-informative with respect to taste then the second set of probabilities calculated with respect to the nutrient-based model are more heavily weighted. For example, if the text-based model yields somewhat non-informative probabilities, such as bitter-38%, salty-42%, umami-10%, sour-0%, spicy-0%, and sweet-0%, then the second set of probabilities calculated with respect to the nutrient-based model may be weighted with around 50% weighting Similarly, if the text-based model yields very uninformative probabilities, such as bitter-16%, sailty-20%, umami-14%, sour-17%, spicy-18%, and sweet-15%, then then the second set of probabilities calculated with respect to the nutrient-based model may be weighted with 100% weighting.

Once a final set of probabilities has been determined, the method 500 continues with a step of determining a most likely taste for the consumable (block 550). Particularly, the processing circuitry/logic 204 is configured to select the taste having the highest probability score. As discussed above with respect to the step 430 of the method 400, the processing circuitry/logic 204 is configured to store the determined taste in the database 220, such as in a data field of, or otherwise in association with, the corresponding consumable record. In one embodiment, if the two most likely tastes have probabilities that are within 20% (or 0.2) of each other, the processing circuitry/logic 204 may be configured to determine that the taste for the consumable is "undecided". In another embodiment, the processing circuitry/logic 204 is configured to instead determine that the taste for the consumable is both of two most likely tastes, thereby labeling the consumable with two taste labels.

Text-Based Model

Figure 6:
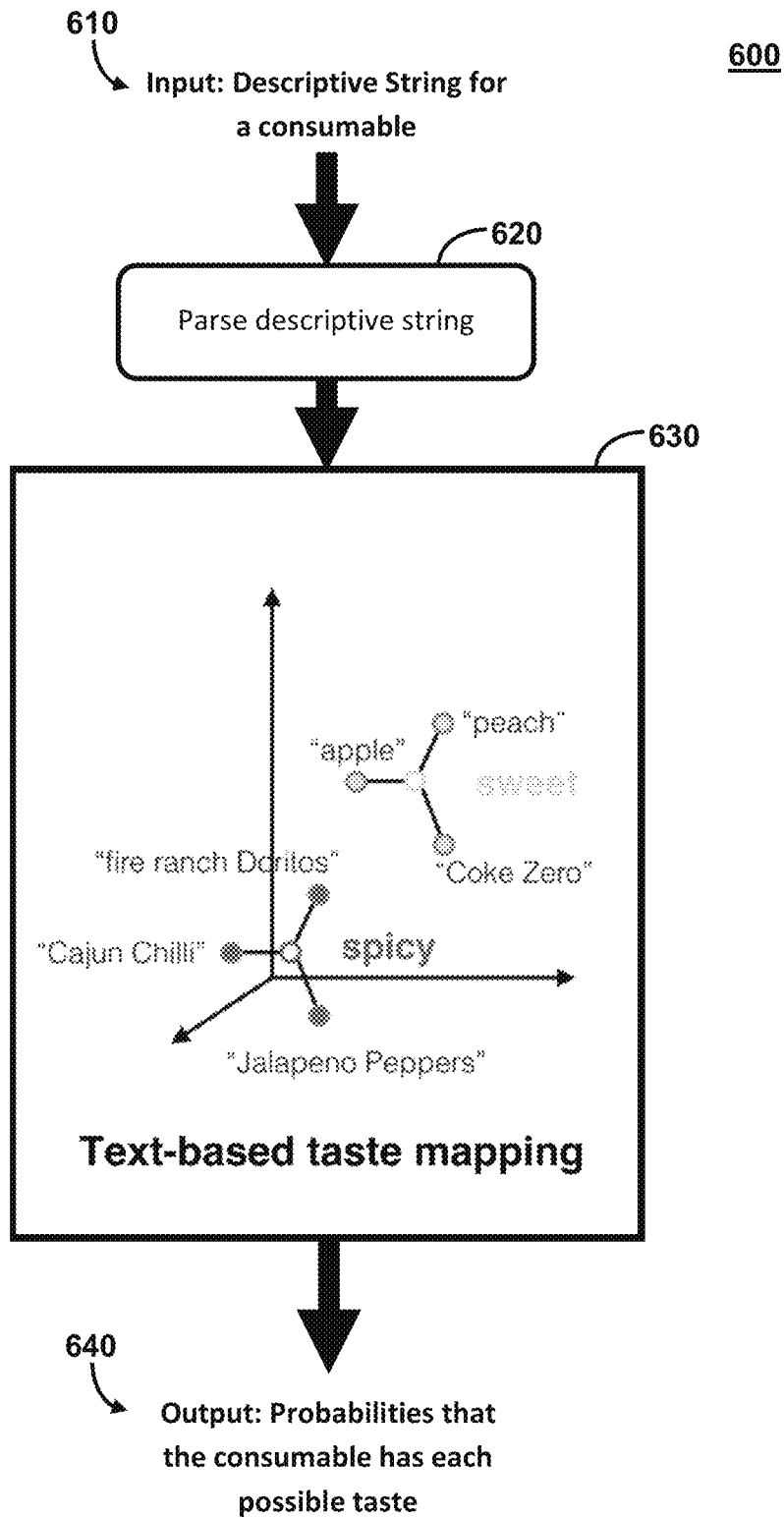
FIG. 6 shows a method of applying a text-based model to calculate probabilities that a consumable has each of the possible tastes.

FIG. 6 shows a method 600 of applying a text-based model to calculate probabilities that a consumable has each of the possible tastes. The method 600 is one exemplary implementation of steps 520 and 530 of the method 500. However, it will be understood by a person having ordinary skill in the art that other methods and/or variations of this method are possible.

The method 600 begins with a descriptive string of a consumable record as an input 610. The method continues with a step of parsing the descriptive string (block 620). Particularly, with respect to the embodiments described in detail herein, the processing circuitry/logic 204 of the system server 200 is configured to vectorize the descriptive string, which is a type of parsing in which the resulting vector is a representation the component parts of the descriptive string and the relationships between those component parts. In one exemplary embodiment, a vector model, such as the so-called word2vec model, is used to transform the descriptive string into a high-dimensional vector, or simply a point in high-dimensional space.

Next, the method 600 includes a step of applying a model to the parsed (or vectorized) descriptive string (block 630). Particularly, the processing circuitry/logic 204 is configured to compare the vectorized descriptive string to a training set of vectors and calculate probabilities that the consumable has each of the possible tastes based on a similarity between the vectorized descriptive string and vectors in the training set. Particularly, in one embodiment, a training set of vectors is created from a training set of consumable records having known tastes. In one embodiment, the training set of consumable records is created based on third-party dataset in which tastes are known. The training set of consumable records is subjected to the vectorization of the step 610 to generate the training set of vectors. In an alternative embodiment, the training set of records and/or vectors may be manually entered by a server-side operator. The processing circuitry/logic 204 is configured to use a weighted k-nearest neighbor algorithm, which is a kind of machine learning pattern recognition, to calculate and provide probabilities that the consumable has each of the possible tastes as an output 640.

For example, if a descriptive string of a consumable record reads "fire ranch Doritos", the vectorization of the descriptive string may be a vector that is most similar to the vectors of "spicy" consumables of the training set of consumable records. In addition, the vectorization of the descriptive string may be somewhat similar to vectors for "sweet" consumables and "salty" consumables of the training set of consumable records. Due to these similarities, application of the weighted k-nearest neighbor algorithm to the vectorization of "fire ranch Doritos" may yield a 70% probability of the consumable being spicy, a 20% probability of the consumable being salty, and a 10% probability of the consumable being sweet.

Nutrient-Based Model

Figure 7:
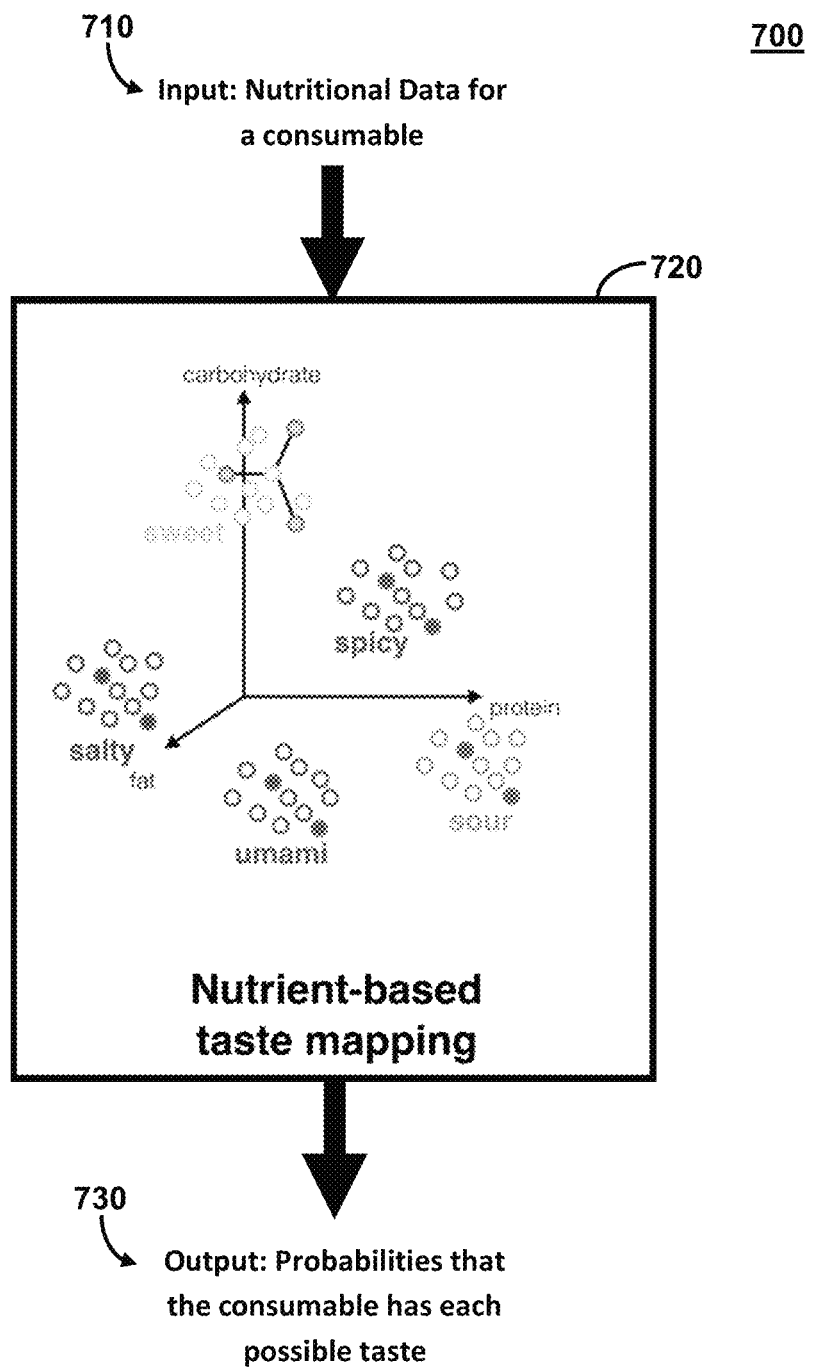
FIG. 7 shows a method of applying a nutrient-based model to calculate probabilities that a consumable has each of the possible tastes.

FIG. 7 shows a method 700 of applying a nutrient-based model to calculate probabilities that a consumable has each of the possible tastes. The method 700 corresponds to one exemplary implementation of steps 525 and 535 of the method 500. However, it will be understood by a person having ordinary skill in the art that other methods and/or variations of this method are possible.

The method 700 begins with nutritional data of a consumable record as an input 710. The method 700 includes the step of applying a model to the nutritional data (block 720). Particularly, with respect to the embodiments described in detail herein, the processing circuitry/logic 204 of the system server 200 is configured to compare the nutritional data to nutritional data of the training set of consumable records and calculate probabilities that the consumable has each of the possible tastes based on a similarity between the nutritional data and the nutritional data of the training set. Alternatively, the training set of records may be manually entered by an operator at the server-side. In one embodiment, the training set of consumable records is the same training set used with respect to the text-based model, which is based on a third-party dataset in which tastes are known. In one embodiment, the processing circuitry/logic 204 is configured to compare the macronutrient contents (i.e. carbohydrates, fats, and proteins) of the consumable to macronutrient contents of the consumable of the training set having known tastes. Particularly, the processing circuitry/logic 204 is configured to use a weighted k-nearest neighbor algorithm to calculate and provide probabilities that the consumable has each of the possible tastes as an output 730.

For example, if a consumable record indicates that a consumable has 15 grams of carbohydrates, 5 grams of fat, and 1 gram of protein, then the consumable may have a macronutrient breakdown that is most similar "sweet" consumables of the training set of consumable records. Additionally, the consumable may have a macronutrient breakdown that is somewhat similar to "salty" consumables of the training set of consumable records. Due to these similarities, application of the weighted k-nearest neighbor algorithm to nutritional data may yield a 70% probability of the consumable being sweet and a 30% probability of the consumable being salty.

Applications for Taste Labels in the Consumable Records Database

In one embodiment, the taste labels associated with the consumable records 224 are used to generate a taste profile for a user. Particularly, the processing circuitry/logic 204 of the system server 200 is configured to receive a consumable log associated with a user profile for a user from the user database 222. The consumable log comprises a plurality of entries corresponding to particular consumable records 224 in the database 220. The processing circuitry/logic 204 is configured to generate a taste profile for the user based on the tastes of the consumable records corresponding to the plurality of entries in the consumable log. The processing circuitry/logic 204 is configured to store the taste profile in the user database 222 in association with the user profile for the user. Alternatively, the taste profile may be similarly generated at the client-side, for example by the processor 308 of the smartphone 110A. The taste profile includes an estimation of the taste preferences of the user based on the consumables that the user has logged. The processing circuitry/logic 204 is configured to transmit the taste profile to a health tracking device 110 associated with the respective user upon request, for his or her viewing.

In some embodiments, the processing circuitry/logic 204 is configured to generate additional information based on the taste profile for a user. For example, in one embodiment, the processing circuitry/logic 204 is configured to generate and transmit a list of recommended consumables for the user. The recommended consumables are consumables that have tastes that align well with the users taste profile, such that the consumables are likely to be palatable to the user. In one embodiment, the recommended consumables comprise a list of healthier alternatives to one or more consumables that the frequently logs. In this way, the taste profile is used to promote healthy choices. In further embodiments, the taste profiles are used to similarly generate other information such as trends in the taste preferences over time, for different meals, and at different times of the month/year.

In some embodiments, the taste profile is used for advertisement targeting. Particularly, in one embodiment, the graphics 228 include a plurality of advertisements stored therein. The processing circuitry/logic 204 is configured to select one or more advertisements based on the taste profile of a user. In other words, the taste profile is used to estimate which of the advertisements is most relevant to a particular user. The processing circuitry/logic 204 is configured to transmit the selected advertisement the health tracking device 110 of the user for presentation to the user. In this way, advertisements may be better targeted to users such that users are presented with advertisements are of greater relevance to his or her taste preferences.

Figure 8:
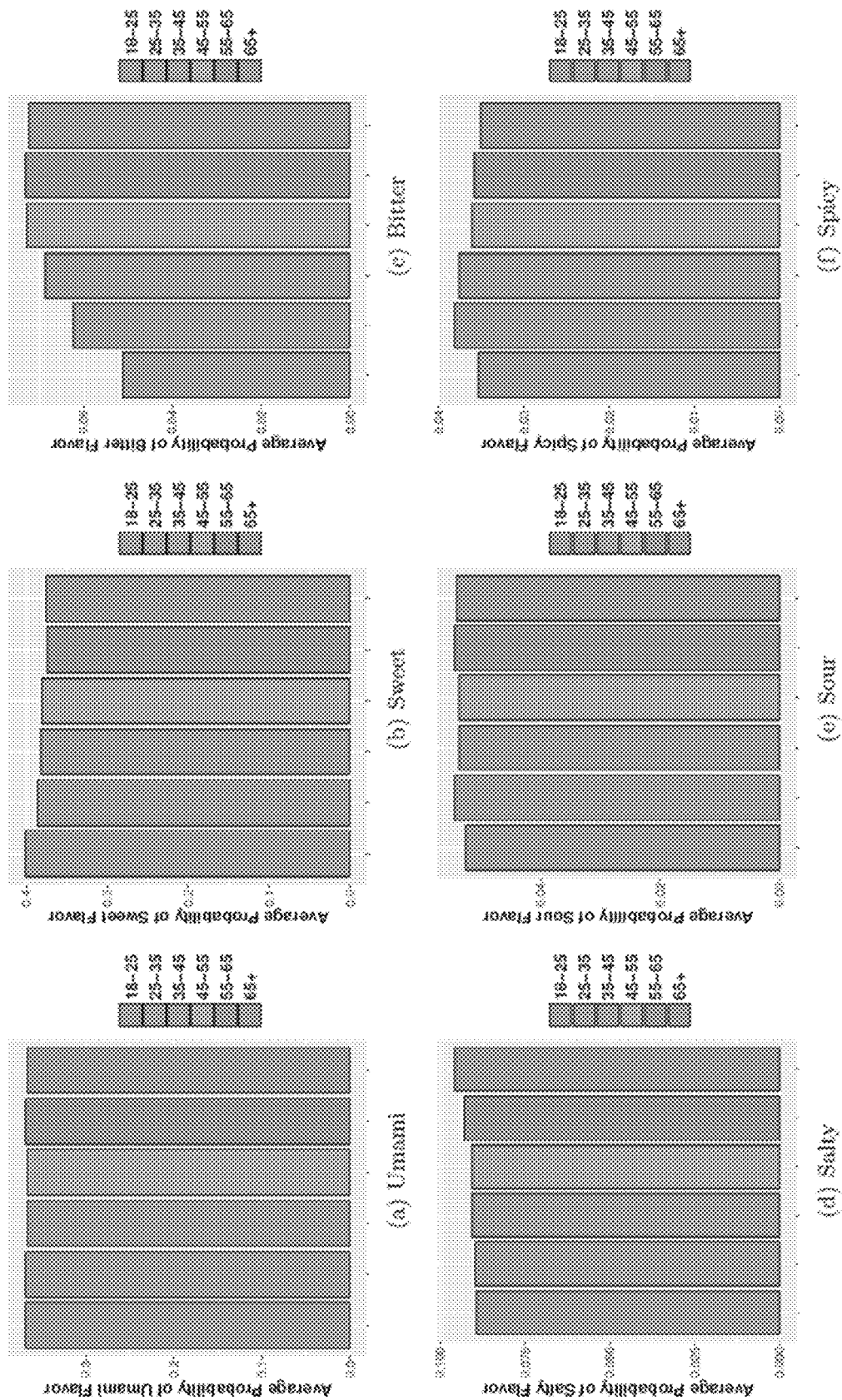
FIG. 8 shows exemplary correlations between taste preferences and different age groups.

In one embodiment, the taste profiles for each user are used for demographic analysis and improved recommendations. For example, FIG. 8 shows exemplary correlations between taste preferences and different age groups. As may be seen, umami and sour taste perceptions appear to be logged similarly, no matter the user's age. Another trend may be found in spicy tastes, where the prevalence of spicy foods starts low in the 18-25 age group, but then peaks in the young adults aged 26-35 after a 7.75% relative increase, before slowly returning to roughly the same as the initial level in the 65 plus age group. By comparison, the three remaining tastes are almost strictly increasing or decreasing with age. Salty and bitter foods increase in their observed data by age by 6.92% and 43.22% respectively, while the prevalence of sweet foods decreases over time by 6.32%. In one embodiment, these observations are used to provide better recommendations and/or select advertisements targeted to users based on an age associated with their user profile, as discussed above.

Figure 9:
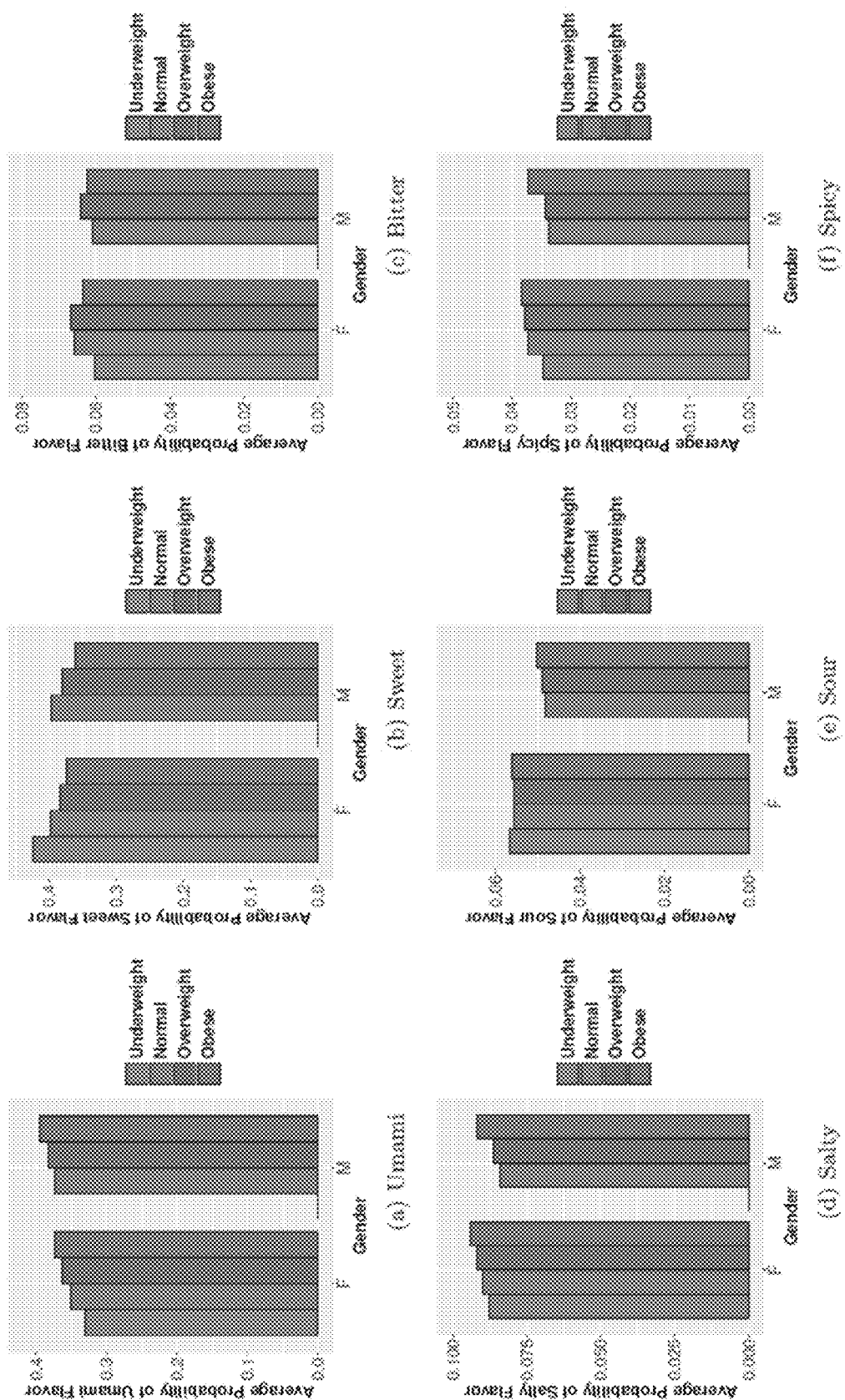
FIG. 9 shows exemplary correlations between taste preferences and observed BMI and gender.

As another example, FIG. 9 shows exemplary correlations between taste preferences and observed BMI and gender. As may be seen, there are mixed or weak trends in the tastes of bitter, sour, and spicy. In contrast, there are much stronger and more noticeable trends in umami and salty tastes, where the prevalence of these tastes increases as BMI increases. For umami, there is a 12:72% increase in females from underweight to obese, and a 5.69% increase in males from normal to obese. The trend in salty meanwhile shows a 7.12% increase in females from underweight to obese, and a 9.15% increase in males from normal to obese. In sweet tastes, the opposite occurs and average probabilities of sweet decrease as the user's BMI increases, with a net 11.86% decrease in females from underweight to obese, and an 8.90% decrease in males from normal to obese. In one embodiment, these observations are used to provide better recommendations and/or select advertisements targeted to users based on a BMI associated with their user profile, as discussed above.

Figure 10:
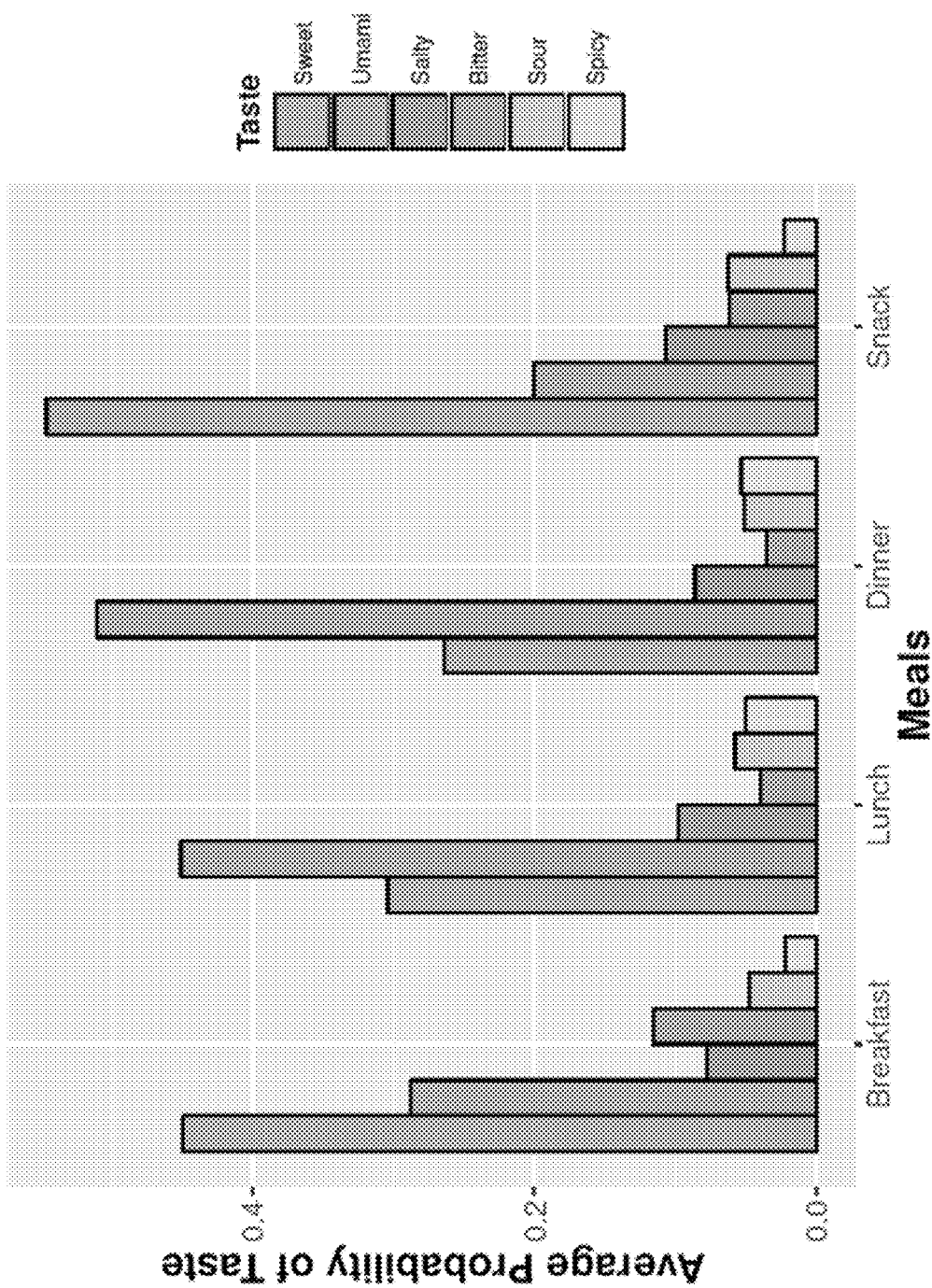
FIG. 10 shows exemplary taste preferences across meals.

As a further example, FIG. 10 shows exemplary taste preferences across meals. As may be seen, breakfast is observed to have comparatively higher proportions of sweet and bitter foods compared to these categories' baselines, perhaps reflecting the prevalence of sugary items, like cereals or fruit juices, and bitter caffeinated drinks, like tea and coffee, in the morning time. Meanwhile, savory foods dominate lunch and dinner, when more meats may be consumed. In one embodiment, these observations are used to enable better recommendations, targeted advertisement selections, and understandings of how to reach healthier outcomes for individuals without upsetting natural meal taste patterns.

Figure 11:
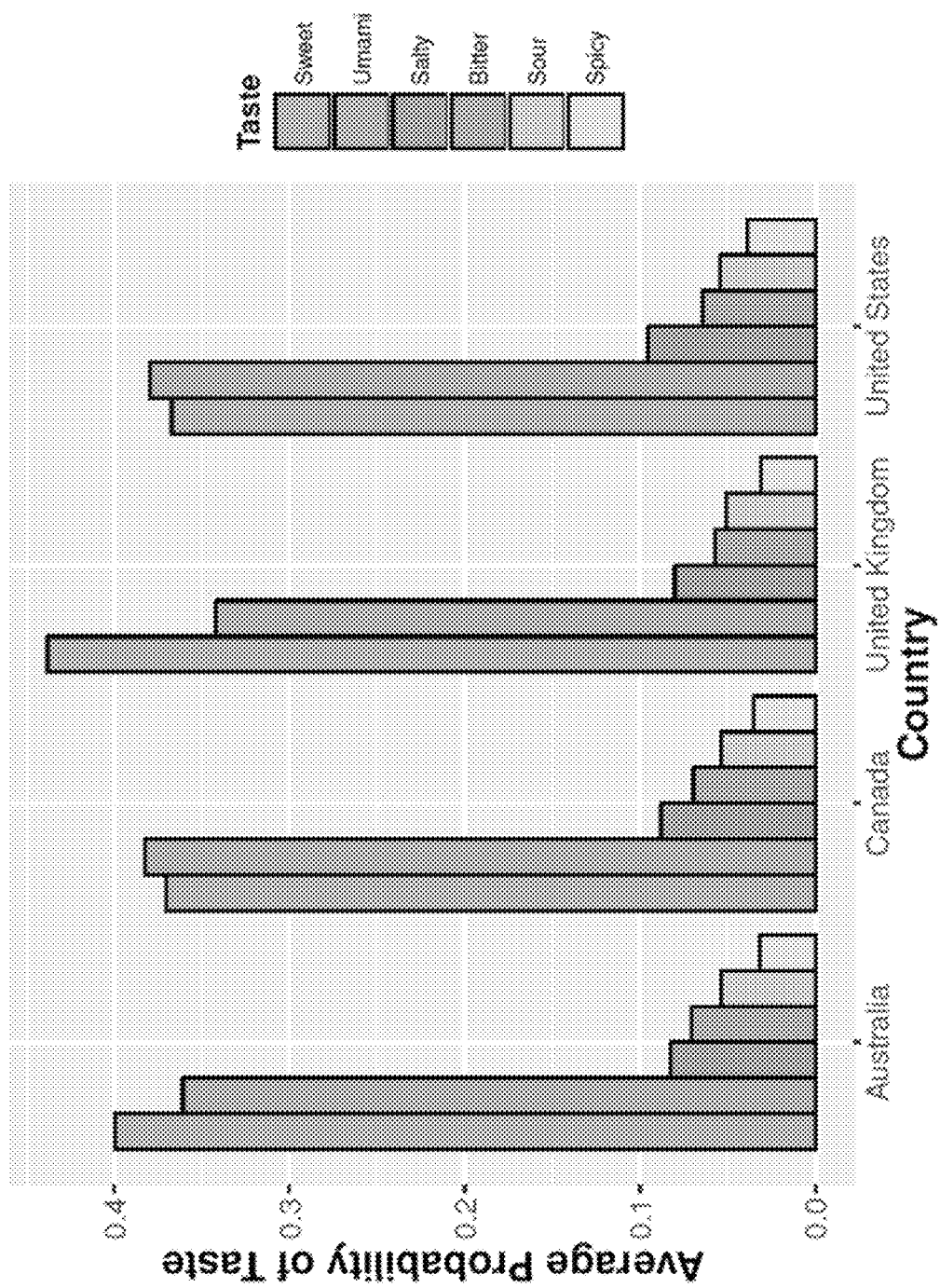
FIG. 11 shows exemplary taste preferences across countries.

As yet another example, FIG. 11 shows exemplary taste preferences across countries. The most significant difference in the taste distributions between these 4 countries corresponds to the high consumption of sweet taste labeled foods among United Kingdom (UK) users, with an average probability of 0.44, when compared to United States (US) users with a probability of 0.37. Furthermore, the consumption of savory foods among UK users, with an average of 0:34, is the smallest compared to other countries, i.e., Australia (0:36), US (0:38) and Canada (0:38). Further, more granular taste distributions may also be determined, such as based on ZIP code, etc. In one embodiment, these observations are used to provide better recommendations and/or select advertisements targeted to users based on a location associated with their user profile, as discussed above.

It will be appreciated that the various ones of the foregoing aspects of the present disclosure, or any parts or functions thereof, may be implemented using hardware, software, firmware, tangible, and non-transitory computer readable or computer usable storage media having instructions stored thereon, or a combination thereof, and may be implemented in one or more computer systems.

The above described system and method solves a technological problem common in industry practice related to accurately categorizing consumable items by taste. Moreover, the above-described system and method improves the functioning of the computer device by enabling taste data to be easily presented to a user in association with a consumable record in health tracking system, thus also allowing the user to easily select consumables that are likely to be of within a typical taste profile for the user. In the foregoing description, various operations may be described as multiple discrete actions or operations in turn, in a manner that may be helpful in understanding the claimed subject matter. However, the order of description should not be construed as to imply that these operations are necessarily order dependent. In particular, these operations may not be performed in the order of presentation. Operations described may be performed in a different order than the described embodiment. Various additional operations may be performed and/or described operations may be omitted in additional embodiments.

The foregoing detailed description of one or more exemplary embodiments of the health tracking system has been presented herein by way of example only and not limitation. It will be recognized that there are advantages to certain individual features and functions described herein that may be obtained without incorporating other features and functions described herein. Moreover, it will be recognized that various alternatives, modifications, variations, or improvements of the above-disclosed exemplary embodiments and other features and functions, or alternatives thereof, may be desirably combined into many other different embodiments, systems or applications. Presently unforeseen or unanticipated alternatives, modifications, variations, or improvements therein may be subsequently made by those skilled in the art which are also intended to be encompassed by the appended claims. Therefore, the spirit and scope of any appended claims should not be limited to the description of the exemplary embodiments contained herein.

What is claimed is:

1. A method for operating a health tracking system, the method comprising:
  receiving a crowd-sourced data record comprising at least a descriptive string and nutritional data regarding a consumable item to which the data record corresponds;
  determining one of a plurality of possible tastes associated to the consumable item by:
    evaluating the nutritional data of the data record to determine an accuracy of the nutritional data with respect to the consumable item,
    when the evaluation of the nutritional data is determined to be accurate, applying a first statistical model to the descriptive string to determine a first set of probabilities that the consumable item has each of the plurality of possible tastes, wherein the plurality of possible tastes includes a plurality of fundamental flavors, applying a second statistical model to the nutritional data to determine a second set of probabilities that the consumable item has each of the plurality of possible tastes, and determining the one of the plurality of possible tastes for the consumable item based on the first set of probabilities and the second set of probabilities, wherein applying the first statistical model comprises (i) vectorizing the descriptive string, (ii) comparing the vectorized descriptive string to a set of training vectors, and (iii) using a weighted k-nearest neighbor algorithm to calculate the first set of probabilities that the consumable item has each of the plurality of possible tastes based on a similarity between the vectorized descriptive string and vectors in the set of training vectors, and
    when the nutritional data is determined to not be accurate, determining the one of the plurality of possible tastes by applying the first statistical model to the descriptive string to determine the first set of probabilities that the consumable item has each of the plurality of possible tastes and determining the one of a plurality of possible tastes for the consumable item based only on the first set of probabilities;

updating a crowd-sourced database in order to associate the determined taste with the data record in the crowd-sourced database;

performing the acts of receiving, determining, and associating updating with respect to each of a plurality data records stored in the crowd-sourced database such that each of the plurality of data records is associated to a taste;

determining a taste profile specific to a user, said taste defined by a probability of each of the fundamental flavors;

generating a list of recommended ones of a plurality of consumable items for the user based at least in part on the determined taste profile specific to the user and the tastes associated with the plurality of data records; and transmitting the generated list of recommended ones of a plurality of consumable items to a health tracking device associated with the user.

2. The method according to claim 1, wherein the nutritional data includes at least a total caloric content and respective amounts of a plurality of macronutrients of the consumable item, and the act of determining the accuracy further comprises comparing the total caloric content to a caloric content representative of the respective amounts of the plurality of macronutrients.

3. The method according to claim 1, further comprising: when the nutritional data is determined to be accurate, weighting an output of the first statistical model, and weighting an output of the second statistical model.

4. The method according to claim 3, wherein a value by which the output of the first statistical model is weighted and a value by which the output of the second statistical model is weighted are dependent on a value of the output of the first statistical model.

5. The method according to claim 1, further comprising:
receiving a list of consumable items, the received list being associated with a user profile stored in the database, the received list containing a plurality of entries corresponding to individual ones of the data records selected by the user; and associating the determined taste profile to the user profile in the database, wherein the determined taste profile specific to the user profile is based on one or more patterns determined from the tastes associated to each of the data records corresponding to the plurality of entries in the received list.

6. The method according to claim 5, further comprising:
selecting individual ones of a plurality of advertisements stored in the database based on the determined taste profile; and transmitting the selected individual ones of the plurality of advertisements to a health tracking device associated with the user profile.

7. The method of claim 1 wherein the plurality of fundamental flavors include two or more of sweet, salty, umami, sour, spicy and bitter.

8. The method of claim 1 wherein the taste profile is defined by a user probability for each of the fundamental flavors.

9. A health tracking system comprising:
a database configured to store a plurality of crowd-sourced data records, each of the plurality of data records comprising at least a descriptive string and nutritional data regarding the consumable item to which the data record corresponds; and a data processor in communication with the database, the data processor being configured to (i) receive one or more of the plurality of data records from the database, (ii) determine a taste aspect for the consumable item to which each of the received ones of the one or more of the plurality of data records corresponds, the determination being based on an evaluation of at least one of the descriptive string and the nutritional data, wherein the taste aspect defines probabilities for each of a plurality of fundamental flavors (iii) generate a list of recommended ones of the plurality of data records based at least in part on the determined taste aspects corresponding to the plurality of data records, and (iv) send the generated list of recommended ones of the plurality of data records to a health tracking device associated with the user;

wherein the evaluation of at least one of the descriptive string and the nutritional data comprises:

for each of the one or more of the plurality of data records, determine whether the nutritional data thereof is accurate with respect to the consumable item;

when it is determined that the nutritional data is accurate, apply a first mathematical model to the nutritional data to calculate a probability that respective ones of the consumable item have a first taste aspect and based on the result thereof, apply a second mathematical model to the descriptive string, wherein applying the second mathematical model comprises (i) vectorizing the descriptive string, (ii) comparing the vectorized descriptive string to a set of training vectors, and (iii) using a weighted k-nearest neighbor algorithm to calculate a first set of probabilities that the consumable item has each of the plurality of possible tastes based on a similarity between the vectorized descriptive string and vectors in the set of training vectors; and when it is determined that the nutritional data is not accurate, apply the second mathematical model to the descriptive string to calculate a probability that respective ones of the consumable item have the first taste aspect.

10. The health tracking system of claim 9, wherein the data processor is further configured to store the determined taste aspects in the database in association with the respective ones of the one or more of the plurality of data records.

11. The health tracking system of claim 9, wherein the at least one of the first and second mathematical models model also comprises a machine learning model which utilizes a training set of data records having known taste aspects associated therewith.

12. The health tracking system of claim 9, wherein applying the first mathematical model also comprises using a weighted k-nearest neighbor algorithm.

13. The health tracking system of claim 9, wherein the application of the second mathematical model to the descriptive string further comprises
vectorize the descriptive string; and
apply applying a pattern recognition model to the vectorized descriptive string.

14. The health tracking system of claim 13, wherein the nutritional data includes at least a total caloric content and respective amounts of a plurality of macronutrients of the consumable item, and wherein determining whether the nutritional data thereof is accurate with respect to the consumable item further comprises comparing the total caloric content to a caloric content representative of respective amounts of the plurality of macronutrients.

15. The health tracking system of claim 13, wherein when the nutritional data is determined to be accurate, weighting an output of the first mathematical model, and weighting an output of the second mathematical model.

16. The health tracking system of claim 15, wherein a value by which the output of the first mathematical model is weighted and a value by which the output of the second mathematical model is weighted are dependent on a value of the output of the first mathematical model.

17. The health tracking system of claim 9, wherein the data processor is further configured to:
receive a list of consumable items, the received list being associated with a user profile stored in the database, the received list containing a plurality of entries corresponding to individual ones of the plurality of data records; and
associate the determined taste aspect to the user profile in the database, wherein the determined taste aspect specific to the user profile is based on one or more patterns determined from the tastes associated to each of the data records corresponding to the plurality of entries in the received list.

18. The health tracking system of claim 9, wherein the data processor is further configured to:
select individual ones of a plurality of advertisements stored in the database based on the user profile; and
transmit the selected individual ones of the plurality of advertisements to a health tracking device associated with the user profile.

19. A non-transitory computer-readable medium for operating a health tracking system, the computer-readable medium having a plurality of instructions stored thereon that, when executed by a processor, cause the processor to:
receive a plurality of crowd-sourced data records from a database, the plurality data records each comprising a descriptive string and nutritional data regarding the respective corresponding consumable;
determine a taste for each of the respective corresponding consumables of the plurality of data records based on at least one of (i) the descriptive string of the data record, and (ii) evaluation of the nutritional data of the data record, the nutritional data including at least a total caloric content and respective amounts of a plurality of macronutrients of the consumable, wherein the determined taste is defined by probabilities that the consumable has each of a plurality of fundamental flavors;
wherein the evaluation of the nutritional data of the data record comprises determining the accuracy of the nutritional data with respect to the consumable by comparing the total caloric content to a caloric content representative of the respective amounts of the plurality of macronutrients, wherein,
when the nutritional data is determined to be accurate, determining the taste by (a) applying a first statistical model to the descriptive string and (b) applying a second statistical model to the nutritional data, wherein applying the first statistical model comprises (i) vectorizing the descriptive string, (ii) comparing the vectorized descriptive string to a set of training vectors, and (iii) using a weighted k-nearest neighbor algorithm to calculate the first set of probabilities that the consumable item has each of the plurality of possible tastes based on a similarity between the vectorized descriptive string and vectors in the set of training vectors; and
when the nutritional data is determined to be inaccurate, determining the taste by applying the first statistical model to the descriptive string and omitting to utilize the nutritional data;
update the database by storing the determined tastes in the database associated to the respective ones of the plurality of data records;
derive a taste profile for a particular user; and
recommend one or more items for consumption and/or provide one or more advertisements to said particular user based at least in part on the derived taste profile and the determined taste for each of the respective corresponding consumables.

20. The non-transitory computer-readable medium of claim 19, wherein the plurality of instructions are further configured to:
utilize said tastes for each of said corresponding consumables to derive the taste profile for the particular user, the taste profile being based at least in part on one or more of:
individual ones of the plurality of data records selected by the particular user, an age of the particular user, and/or a gender of the particular user.

* * * * *